United States Patent

Belly et al.

[11] Patent Number: 6,090,568
[45] Date of Patent: Jul. 18, 2000

[54] FORMAT FOR MINIMIZING INTERFERENCES IN CHEMILUMINESCENT THIN-FILM IMMUNOASSAYS

[75] Inventors: Richard Troconis Belly, Ithaca; Caroline Erdrich, Fairport; Richard Calvin Sutton, Rochester, all of N.Y.

[73] Assignee: Clinical Diagnostic Systems, Inc., Rochester, N.Y.

[21] Appl. No.: 08/906,007

[22] Filed: Aug. 4, 1997

Related U.S. Application Data

[63] Continuation of application No. 08/540,994, Oct. 11, 1995, abandoned, which is a continuation of application No. 08/220,324, Mar. 30, 1994, abandoned.

[51] Int. Cl.[7] .................................................. G01N 33/53
[52] U.S. Cl. ........................ 435/7.92; 435/7.93; 435/7.94; 435/7.95; 435/962; 435/968; 435/969; 435/970; 436/518; 436/523; 436/529; 436/810; 436/825
[58] Field of Search ........................ 435/7.9–7.95, 435/25, 28, 805, 962, 968–970; 436/518, 523, 529, 805, 810, 825; 422/52, 55, 56, 57, 60

[56] References Cited

U.S. PATENT DOCUMENTS

| | | | |
|---|---|---|---|
| 4,258,001 | 3/1981 | Pierce et al. | 422/56 |
| 4,488,084 | 12/1984 | Lindfors et al. | 313/506 |
| 4,578,245 | 3/1986 | Arai et al. | 422/56 |
| 4,670,381 | 6/1987 | Frickey et al. | 435/7 |
| 4,729,950 | 3/1988 | Kricka et al. | 435/28 |
| 4,870,005 | 9/1989 | Akiyoshi et al. | 435/7 |
| 4,916,059 | 4/1990 | Kageyama et al. | 435/15 |
| 4,975,366 | 12/1990 | Sudo et al. | 435/7 |
| 5,066,462 | 11/1991 | Kawasaki et al. | 422/56 |
| 5,120,643 | 6/1992 | Ching et al. | 435/7.92 |
| 5,122,451 | 6/1992 | Tanaka et al. | 435/74 |
| 5,152,962 | 10/1992 | Lackie | 422/681 |
| 5,244,815 | 9/1993 | Guirguis | 436/530 |
| 5,252,496 | 10/1993 | Kang et al. | 436/529 |
| 5,279,940 | 1/1994 | Kissel | 435/6 |
| 5,290,514 | 3/1994 | Tanaka et al. | 422/56 |
| 5,441,894 | 8/1995 | Coleman et al. | 436/518 |
| 5,492,674 | 2/1996 | Meserol | 422/82.08 |

FOREIGN PATENT DOCUMENTS

| | | | |
|---|---|---|---|
| 0 051 183 | 5/1982 | European Pat. Off. | 436/518 |
| 0 487 165 A3 | 5/1992 | European Pat. Off. | 422/56 |
| 0 587 222A3 | 3/1994 | European Pat. Off. | 436/518 |
| WO 90/00572 | 1/1990 | WIPO | 422/82.05 |
| WO 94/25160 | 11/1994 | WIPO | 436/518 |

OTHER PUBLICATIONS

Translation of Kokai Patent Application No. SHO 61[1986]–126470 Corresponding to Kawakatsu et al Application SHO 59[1984]–248093.

*Primary Examiner*—Carol A. Spiegel
*Attorney, Agent, or Firm*—James H. Harrington; Charles Limuti

[57] ABSTRACT

A multilayer dry immunoassay element comprising 1) a spreading layer having a sample application area and a signal read area and 2) a separate receptor layer residing on 3) a radiation-transmissive support characterized in that the spreading layer contains a light absorbing material.

4 Claims, 1 Drawing Sheet

FORMAT FOR MINIMIZING INTERFERENCES IN CHEMILUMINESCENT THIN-FILM IMMUNOASSAYS

This is a CONTINUATION of application Ser. No. 08/540,994, filed Oct. 11, 1995, now abandoned, which is a CONTINUATION of application Ser. No. 08/220,324, filed Mar. 30, 1994, now abandoned.

FIELD OF THE INVENTION

This invention relates to clinical chemistry, particularly immunoassay elements and methods.

BACKGROUND OF THE INVENTION

Immunoassays, which take advantage of natural immunological reactions, have found wide-spread use as analytical techniques in clinical chemistry. Because of the specificity of the reactions, they are particularly advantageous in quantifying biological analytes that are present in very low concentration in biological fluids. Such analytes include, for example, antigen, antibodies, therapeutic drugs, narcotics, enzymes, hormones, proteins, etc.

The analyte, which is the target of the assay is referred to herein as the ligand, and the labeled analyte is referred to as the labeled ligand (including immunocompetent derivatives and analogs of such ligand). Compounds which specifically recognize the ligand and the labeled ligand and react to form complexes with them are referred to herein as receptors. The receptor and the ligand or labeled ligand form a conjugate pair. Any member of the pair can function as a receptor or a ligand.

In competitive binding immunoassays, a labeled ligand is placed in competition with unlabeled ligand for reaction with a fixed amount of the appropriate receptor. Unknown concentrations of the ligand can be determined from the measured signal of either the bound or unbound (i.e. free) labeled ligand. The reaction proceeds as follows:

ligand+labeled ligand+receptor<=>ligand-receptor+
labeled ligand-receptor.

In an alternative type of immunological assay, commonly referred to as a sandwich assay, a ligand (antibody or antigen analyte) is contacted with a receptor to cause the ligand to bind to the receptor. This complex is then contacted with a solution of a labeled binding agent, such as an antibody, which reacts with the bound ligand. The amount of bound labeled binding agent is thus directly proportional to the amount of bound ligand.

Dry immunoassay analytical elements are known. In general such elements comprise receptors, such as antibodies for a ligand, immobilized in a particulate layer. In addition the element usually contains a reagent system that through interaction with a bound or unbound species results in a signal that can be correlated to the concentration of ligand in a sample. In use the sample is manually combined with an enzyme labeled ligand and applied to the element. After a time a wash solution containing a substrate for the labeled ligand is applied to the particulate layer. The substrate is catalyzed by the enzyme label to form a reaction product that ultimately causes a signal, such as chemiluminescence, to develop that can be correlated to the concentration of the ligand in the sample. Signal development systems are known for other known conventional labels such as radioactive tags, chromophores, fluorophores, stable free radicals, and enzyme cofactors, inhibitors and allosteric effectors.

One problem that occurs in immunoassays of serum samples is background interference caused by the presence of hemoglobin arising from red blood cell lysis. Hemoglobin is a pseudoperoxidase. As such it catalyzes oxidation of a leuco dye, or chemiluminescent compound precursors, similarly to peroxidase enzyme labels producing a background signal. This background signal causes assay results to lack precision and accuracy.

This problem is aggravated when detection and quantification at picomolar concentrations are required for many diagnostically important serum hormones and cancer markers. Among the medically important hormones present in serum at picomolar concentration are aldosterone, insulin, thyroid stimulating hormone (TSH), angiotensin, ocytocin, parathyroid hormone (PTH), growth hormone, adrenocorticotrophic hormone (ACTH), and vasopressin. To perform immunoassay for serum analytes present at picomolar concentration, a sensitive detection chemistry such as fluorescence or chemiluminescence is needed. Because of the sensitivity of this type of detection chemistry, background due to hemoglobin pseudoperoxidase activity, unbound label or chemical interferents present in the serum sample have to be thoroughly removed.

SUMMARY OF THE INVENTION

The present invention provides a multilayer dry immunoassay element comprising 1) a spreading layer having a sample application area and a signal read area and 2) a separate receptor layer residing on 3) a radiation-transmissive support characterized in that the spreading layer contains a light absorbing material. This element greatly reduces the interference caused by hemoglobin in serum samples, thereby increasing the signal to noise ratio, particularly for assays employing chemiluminescence detection and measurement.

The above element is particularly useful in immunoassays for ligands present in concentrations below about 1 nanomolar when a separate layer of an absorbent material is positioned (a) in contact with the spreading layer;

(b) is positioned adjacent to the periphery of the sample application area in the spreading layer; and (c) absorbs wash fluid that contains soluble interferents and unbound label away from the signal read area.

DETAILS OF THE INVENTION

Figure 1:
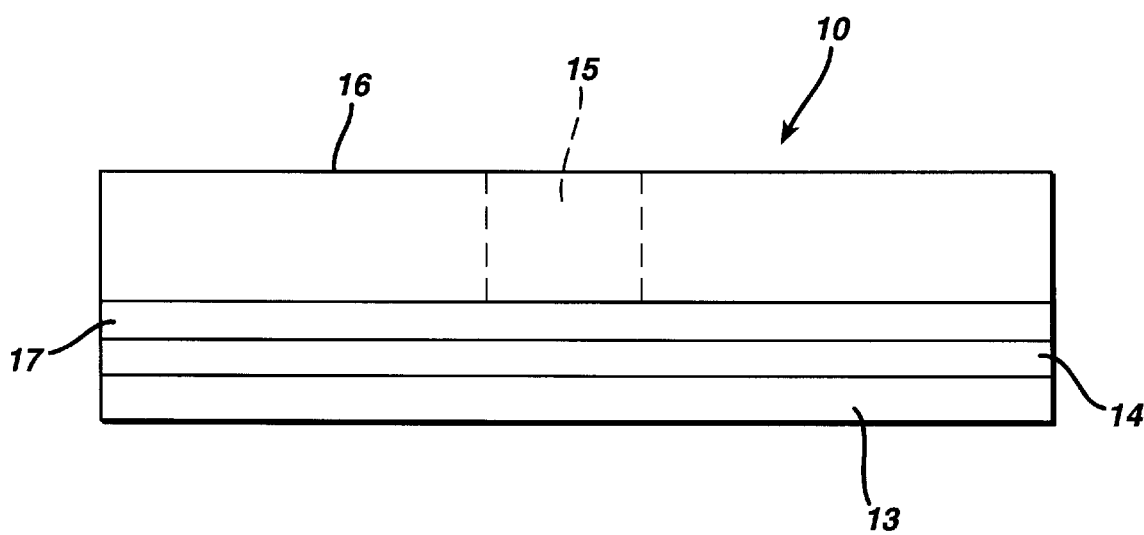
FIG. 1 is an embodiment of the invention having a separate absorptive layer.

Useful spreading layers, including bead spreading layers are disclosed in U.S. Pat. Nos. 4,670,381; 4,258,001 and 4,430,436. Particularly useful spreading layers are those having a particulate structure formed by organo-polymeric particles and a polymeric adhesive for those particles described in U.S. Pat. No. 4,258,001. The organo-polymeric particles useful in the spreading layer are generally heat-stable, spherical beads having a particle size in the range of from about 10 to 40 μm in diameter or even smaller. The sample application area serves as the signal read area in embodiments of the invention in which the signal is read from the top of the spreading layer. In embodiments in which the signal is read from the backside of the element through the radiation transmissive support the signal read area is located on the spreading layer, between the receptor layer and the spreading layer, directly opposite the sample application area.

It is novel and unobvious for spreading layers to contain from 10 to 100 percent, preferably 50 to 100 percent, of particles or beads containing light absorbing materials. Light absorbing materials include carbon black, dyes and pigments designed to absorb light of a desired wavelength.

The particles or beads can be composed of a wide variety of organic polymers, including both natural and synthetic polymers, having the requisite properties. Preferably, however, they are composed of one or more addition polymers described in the aforementioned patents.

The separate receptor layer is prepared and coated over the radiation-transmissive support. A separate radiation reflecting layer can be coated between the spreading layer and the receptor layer to improve the signal area monitored through the support. The receptors can be covalently bonded to polymer particles through surface reactive groups on the receptor (nucleophilic free amino groups and sulfhydryl groups).

A general procedure for attaching receptors to the small polymer beads includes covalently attaching the selected receptor to the beads using generally known reactions. With many pendant groups for example the haloalkyl, 2-substituted activated ethylsulfonyl and vinylsulfonyl, the receptor can be directly attached to the beads. Generally, the beads are mixed with the receptor in an aqueous buffered solution (pH generally from about 5 to about 10) and a concentration of from about 0.1 to about 40 weight percent polymer particles (preferably from about 0.1 to about 10 weight percent). The amount of receptor is at a ratio to polymer of from about 0.1:1000 to about 1:10, and preferably from about 1:100 to about 1:10. Mixing is carried out at a temperature in the range of from about 5 to about 50° C., and preferably at from about 5 to about 40° C., for from about 0.5 to about 48 hours. Any suitable buffer can be used.

In some instances, the pendant reactive groups on the outer surface must be modified or activated in order to cause covalent attachment of the ligand. For example, carboxyl groups must be activated using known carbodiimide or carbamoylonium chemistry, described in EP 308235 published Jul. 22, 1992 and U.S. Pat. No. 5,155,166; or dication ethers known from U.S. Pat. No. 5,266,500.

The attachment of the receptor to carboxyl group-containing monodispersed polymer beads, however, is carried out in two steps, the first of which involves contacting an aqueous suspension of the particles with a carbodiimide or a carbamoylonium or dication ether compound to produce reactive intermediate polymer particles having intermediate reactive groups in place of the carboxyl groups. This step is carried out at a suitable pH using suitable acids or buffers to provide the desired pH. Generally, the pH is less than 6, but this is not critical as long as the reaction can proceed. More likely, the pH is between about 3.5 and about 7. The molar ratio of carbodiimide or carbamoylonium compound or dication ether to the carboxyl groups on the surface of the particles is from about 10:1 to 500:1.

In the second step of the method, the reactive intermediate formed in the first step is contacted with a reactive amine- or sulfhydryl-group containing receptor. A covalent linkage is thereby formed between the particles and the receptor. The weight ratio of the receptor to the polymeric particles is generally from about 1:1000 to about 1:1, and preferably from about 1:100 to about 1:10.

In other instances, an epoxy group on the outer surface can be hydrolyzed to form a diol compound capable of reacting with cyanogen bromide which can act as a coupling agent for amine groups in the immunological species. Aldehydes can react directly with amines to form a Schiff's base which can be subsequently reduced to form a covalent link. Alternatively, the aldehyde can be oxidized to an acid and chemistry identified above for carboxyl groups can be used to form an amide linkage.

Any reactive amine- or sulfhydryl-containing receptor can be attached to the polymeric beads as long as that receptor contains a reactive amine or sulfhydryl group, respectively, which will react with the reactive groups on the polymer or with the intermediate formed by the reaction of a carbodiimide or a carbamoylonium or dication ether compound with carboxyl groups on the particles in the case which the polymer has reactive carboxyl groups.

The small polymer beads having reactive groups that readily react directly with the amine or sulfhydryl groups on the receptors are simply mixed with the receptors, in an appropriate buffer if necessary, and allowed to react.

Polymers from which beads for the receptor can be selected include the following: poly(m & p-chloromethylstyrene), poly(styrene-co-m & p-chloromethylstyrene-co-2-hydroxyethyl acrylate) (67:30:3 molar ratio), poly(styrene-co-m & p-chloroethylsulfonylmethylstyrene) (95.5:4.5 molar ratio), poly{styrene-co-N-[m & p-(2-chloroethylsulfonylmethyl) phenyl]acrylamide} (99.3:0.7 molar ratio), poly(m & p-chloromethylstyrene-co-methacrylic acid) (95:5, 98:2 and 99.8:0.2 molar ratio), poly(styrene-co-m & p-chloroethylsulfonylmethylstyrene-co-methacrylic acid) (93.5:4.5:2 molar ratio), poly{styrene-co-N-[m & p-(2-chloroethylsulfonylmethyl)phenyl]acrylamide-co-methacrylic acid} (97.3:0.7:2 molar ratio), poly(styrene-co-m & p-chloromethylstyrene) (70:30 molar ratio), poly [styrene-co-3-(p-vinylbenzylthio)propionic acid] (97.6/2.4 molar ratio), poly(styrene-co-vinylbenzyl chloride-co-acrylic acid) (85:10:5 molar ratio), poly(styrene-co-acrylic acid) (99:1 molar ratio), poly(styrene-co-methacrylic acid) (90:10 molar ratio), poly(styrene-co-acrylic acid-co-m & p-divinylbenzene) (89:10:1 molar ratio), poly(styrene-co-2-carboxyethyl acrylate) (90:10 molar ratio), poly(methyl methacrylate-co-acrylic acid) (70:30 molar ratio), poly(styrene-co-m & p-vinylbenzaldehyde) (95:5 molar ratio), and poly(styrene-co-m & p-vinylbenzaldehyde-co-methacrylic acid) (93:5:2 molar ratio).

Preferred polymeric binders for the receptor layer are described generally in Canadian patent 1,240,445 and are expressly incorporated herein by reference. Useful polymers are chill-gelable polymers comprising from about 30 to 97 weight percent of polymerized N-alkyl substituted acrylamide such as N-isopropylacrylamide. Other useful N-alkyl-substituted acrylamides include N-n-butylacrylamide, N,N-diethylacrylamide and N-n-propylacrylamide. Polymer binders comprising 60 to 97 weight percent of polymerized N-isopropylacrylamide are used in the examples to clarify the utility of these binders.

The polymer binder also comprises from about 3 to 25 weight percent of one or more polymerized crosslinking monomers having at least two addition-polymerizable groups per molecule. These crosslinking monomers are generally well known in the art. The preferred crosslinking monomers contain acrylamido or methacrylamido groups to facilitate polymerization with the N-alkyl-substituted acrylamides.

Examples of useful crosslinking monomers include:

N,N'-methylenebisacrylamide;

N,N'-methylenebismethacrylamide;

ethylene dimethacrylate;
2,2-dimethyl-1,3-propylene diacrylate;
divinylbenzene;
mono[2,3-bis(methacryloyloxy)propyl] phosphate;
N,N'-bis(methacryloyl)urea;
triallyl cyanurate;
allyl acrylate;
allyl methacrylate;
N-allylmethacrylamide;
4,4'-isopropylidenediphenylene diacrylate;
1,3-butylene diacrylate;
1,4-cyclohexylenedimethylene dimethacrylate;
2,2'-oxydiethylene dimethacrylate;
divinyloxymethane;
ethylene diacrylate;
ethylidene diacrylate;
propylidene dimethacrylate;
1,6-diacrylamidohexane;
1,6-hexamethylene diacrylate;
1,6-hexamethylene dimethacrylate;
phenylethylene dimethacrylate;
tetramethylene dimethacrylate;
2,2,2-trichloroethylidene dimethacrylate;
ethylenebis(oxyethylene) diacrylate;
ethylenebis(oxyethylene) dimethacrylate;
ethylidyne trimethacrylate;
propylidyne triacrylate;
vinyl allyloxyacetate;
1-vinyloxy-2-allyloxyethane;
2-crotonoyloxyethyl methacrylate;
diallyl phthalate; and
2-(5-phenyl-2,4-pentadienoyloxy)ethyl methacrylate.

The above preferred polymeric binders for the receptor layer can include 0 to 60 weight percent of polymerized hydrophilic monomers. Amounts of 0.5 to 35 weight percent are also useful. Hydrophilic monomers are disclosed in Canadian patent 1,240,445. In particular such monomers have one or more groups selected from hydroxy, pyrrolidone, amine, amide, carboxy, sulfo, carboxylate salt, sulfonate salt and sulfate salt groups. Generally the counter ions of the salt groups are alkali metal or ammonium. Useful hydrophilic monomers are acrylic acid and methacrylic acid and their sodium salts, sodium 2-acrylamido-2-methylpropanesulfonate, 2-hydroxyethyl acrylate, 2-hydroxyethyl methacrylate, 2-hydroxypropyl acrylate, 2-hydroxypropyl methacrylate and glyceryl methacrylate.

Useful polymeric binders for the receptor layer also include:
poly(vinyl alcohol);
bovine serum albumin;
acacia gum;
homopolymers of poly-N-vinylpyrrolidone having a molecular weight in the range 8000 to 400,000; and
water-soluble vinyl addition copolymers having two or more monomers selected from the group consisting of acrylamide, methacrylamide, N-alkyl-substituted acrylamides, N-alkyl substituted methacrylamides, 1-vinylimidazole, 2-alkyl substituted-1-vinylimidazoles, 2-hydroxyalkyl substituted-1vinylimidazoles, N-vinylpyrrolidone, hydroxyalkyl acrylates, hydroxyalkyl methacrylates, acrylic acid, and methacrylic acid; wherein alkyl and hydroxyalkyl in the copolymers has 1 to 6 carbon atoms such as methyl ethyl, propyl and hexyl.

An embodiment of the invention which adds great wash volume capacity of above 12 $\mu$L up to about 100 $\mu$L comprises a separate absorbent layer. This absorbent layer minimizes pseudopositive or pseudonegative results in assays for low level analytes. In FIG. 1 there is shown, generally at 10, an embodiment of an element of the present invention with an absorbent layer. The element comprises a receptor layer 14 carried on the radiation transmissive support 13 and having a sample application area 15, an absorbent material 16 in contact with a spreading layer 17. The absorbent layer is positioned adjacent to at least a portion of the periphery of sample application area 15. Light absorbing means can be included in the separate absorbent layer. The separate absorbent layer makes it possible to substantially increase wash volume for performing thin film immunoassays. This increases the sensitivity of the assay by removing unbound label and soluble interferents from the signal read area. In this embodiment the signal read area is positioned between the receptor layer and the spread layer because the read signal will be read with a reflectometer positioned in front of the radiation transmissive support. Absorbent material can be comprised of materials such as glass microfibers, paper, sponge, fabric, plastic or the like, so long as the material is capable of absorbing liquids. The ability to absorb liquid may be influenced by pretreating the absorbent material, for example, with additional absorbent enhancing agents such as wetting agents or the introduction of functional groups. Optionally, the absorbent can be sealed with paraffin or other water-impermeable material around the area immediately adjacent the signal read area. This may increase wash efficiency by not allowing fluid to be absorbed prior to permeation through the matrix.

In the embodiment of FIG. 1, analytical element 10 comprises at least one porous spreading layer. It is desirable that the spreading layer be isotropically porous, meaning that the porosity is the same in each direction in the layer as caused by interconnected spaces or pores between particles, fibers or polymeric strands.

In one illustrative embodiment, in performing an immunoassay using the analytical element with the separate absorbent layer, a sample of serum or other fluid is spotted on the sample application area of the spreading layer. After an incubation period, allowing for the immunological binding reactions to occur (i.e., competitive or sandwich assay), the sample application area is washed with up to about 250 $\mu$L of wash solution, preferably at a metered rate of up to 10 $\mu$L/sec, and most preferably 1 $\mu$L/sec. It is preferred that the detection solution be used as the wash solution. However, the signal-generating substrate can be added as a separate fluid after the wash step. Upon wetting, the absorbent material of the element absorbs the wash fluid containing soluble interferents and unbound label away from the signal read area of the reagent matrix, thereby decreasing background interference from the signal read area. Further, the light absorbing means associated with the absorbent material absorbs or blocks background signal generated by washed, removed label and other interferents from outside the signal read area, thereby preventing background signal from moving back into the signal read area monitored through the transparent support. This increases efficiency and sensitivity of the immunoassay. Thereafter, the detection signal (i.e., chemiluminescence, fluoroescence or colorimetry) is measured to determine analyte concentration.

Ligands labeled with enzymes such as horseradish peroxidase, chromophores, fluorescent and chemiluminescent compounds can be directly measurable, e.g. by fluorescence, ultraviolet spectroscopy or other spectroscopic means. Methods of using such labels in detecting and measuring the target ligand are well known to those skilled in the art. For illustrative purposes, the preferred detection chemistry is enhanced chemiluminescence according to the following reaction:

$$\text{Luminol} + H_2O_2 \xrightarrow[\text{ETA}]{\text{HRP}} \text{Aminophthalate} + \text{Light}$$

where ETA (electron transfer agent) is an aniline or phenol such as 4'-Hydroxyacetanilide (4'-HA) and HRP is horseradish peroxidase.

The labeled ligand or ligand analog recognized by the receptor in the separate receptor layer can be incorporated into the spreading layer prior to use, or added at the time of the assay. Preferably, both are incorporated into the spreading layer prior to use.

The immunoassay can be manual or automated. In general, the amount of a ligand in a liquid is determined by taking the element from a supply roll, chip packet or other source and physically contacting a finite area of the spreading layer with a sample of the liquid, e.g. 1 to 100 $\mu$L. The finite area which is contacted is generally no more than about 150 mm$^2$.

The element is carried on a suitable radiation-transmissive support through which the immunoassay signal is detected and quantified as is well known in the art. The support can be any suitable dimensionally stable, and preferably, non-porous and transparent (i.e. radiation transmissive) material which transmits electromagnetic radiation of a wavelength between about 200 and about 900 nm. A support of choice for a particular element should be compatible with the intended mode of detection (reflection, transmission or fluorescence spectroscopy). Useful support materials include polystyrene, polyesters [e.g. poly(ethylene terephthalate)], polycarbonates, cellulose esters (e.g. cellulose acetate), etc.

The following examples demonstrate the effectiveness of the spreading layer containing light absorbing means. The material names and acronyms used in the elements and solutions of the examples have the following meanings:
Tris: Tris(hydroxymethyl)aminomethane buffer.
DTPA: Diethylenetriaminepentaacetic acid.
Polymer Adhesive: Poly(methyl acrylate-co-sodium 2-acrylamido-2-methylpropanesulfonate-co-2-acetoacetoxyethyl methacrylate).
Anti TSH Capture Antibody/Beads: Latex polymer particles of poly[styrene-co-3-(p-vinylbenzylthiopropionic acid] having anti TSH (thyroid stimulating hormone) capture antibody covalently bound thereto via amide groups formed from the polymer carboxyl groups and antibody amine groups.
Polymer Binder: A microgel of poly(N-isopropylacrylamide-co-sodium 2-acrylamido-2-methylpropanesulfonate-co-N,N'-methylenebisacrylamide) (weight ratio 80/10/10).
TRITON X-100: An octylphenoxy polyethoxy ethanol surfactant sold by Union Carbide Chem. and Plastics Co. (TRITON X-100).
Hardener: Bis(vinylsulfonylmethyl) ether (BVSME).
CTAC: N-Cetyl-N,N,N-trimethylammonium chloride.

EXAMPLE 1

Several machine-coated elements were prepared to evaluate the effect of a spreading layer containing black beads on the chemiluminescence light signal due to hemoglobin pseudoperoxidase activity. The element had the following general structure and composition.

| Layer | Material* | Dry Coverage (g/m$^2$) |
|---|---|---|
| (2) Bead Spread Layer | Tris (0.1 M, pH 8.0) | 1.21 |
| | DTPA (10$^{-4}$ M) | 0.004 |
| | Polymer beads | 130 |
| | Polymer Adhesive | 2.583 |
| (1) Gel Pad | Gelatin | 10.0 |
| | Tris (0.2 M, pH 8.0) | 2.4 |
| | DTPA (10$^{-4}$ M) | 0.004 |
| | Triton X-100 | 0.020 |
| | Hardener | 0.15 |
| Support | Poly (ethylene terephthalate) | |

Five elements according to the above configuration and components were prepared. Each element also included a separate absorbent layer situated above and in contact with the spreading layer as previously described herein. The resulting element had a configuration according to FIG. 1. The elements differed from each other according to the polymer beads in the bead spread layer. The different beads are described below:

A. All white beads of poly(vinyltoluene-co-methacrylic acid) (PVM-W) having an average diameter of about 30 $\mu$m.

B. A mixture of the white (PVM-W) polymer particles of A (50%, coverage 65 g/m$^2$) and the same type of polymer beads having 1.4% carbon black incorporated therein (PVM-B) (50%, coverage 65 g/m$^2$).

C. A mixture of the white (PVM-W) polymer beads of A (50%, coverage 65 g/m$^2$) and poly(styrene-co-methacrylic acid) (99/1) beads having 1.4% carbon black incorporated therein (PS-B) and having an average particle size of about 24 $\mu$m (50%, coverage 65 g/m$^2$).

D. All black (PS-B) beads described in C above.

E. All black (PVM-B) beads described in B above.

The following solutions were provided for use in this example:
Serum: Goat serum purchased from GIBCO.
Hemoglobin/Serum Solution: Hemoglobin (Sigma Chemical Co., cat. H7379), containing 75% methemoglobin, was reconstituted to 10 mg/mL in distilled water. Aliquots were stored frozen and diluted to 100 mg/dL with goat serum, 1 hour prior to use.
Chemiluminescent (Luminol) Signal Reagent/Wash Fluid was prepared at the time of use:
Tris, pH 8.0 0.05 M
Luminol 1 mM
3'-Chloro-4'-hydroxyacetanilide 150 $\mu$M
Hydrogen Peroxide 2 $\mu$M
DTPA 100 $\mu$M
CTAC 0.1%
Procedure The spreading layer of each element was spotted with 10 $\mu$L of the hemoglobin/serum solution, and then incubated for 5 minutes at 37° C. in a covered moist Petrie dish set in a water bath. The hemoglobin binds to the components of the bead spreading layer. The slide was then washed with 100 $\mu$L of freshly prepared chemiluminescent signal reagent/wash solution, at a wash rate of 1.0 $\mu$L/sec. After incubation, the coating was removed from the slide mount so that it could properly fit into a luminometer, and chemiluminescence (CL) from the element was measured on a Turner Model TD20E luminometer, taking 5 reads 1 minute apart over a 4-minute period, the first read at time zero. Each read is a 10-second integration. The 4-minute read is used for data workup. The results are recorded in Table I.

TABLE I

4 Minute Chemiluminescent Signal

| Coating/ SDI 3323- | % Black/White Beads in Spreading Layer | 2 Replicates | Mean | % of Hemoglobin Observed |
|---|---|---|---|---|
| A | 100% White PVM-W | 71.5 87.8 | 79.7 | 100 |
| E | 100% Black PVM-B | 3.4 2.9 | 3.2 | 4 |
| B | 50% Black PVM-B | 9.6 9.5 | 9.6 | 12 |
| D | 100% Black PS-B | 3.4 3.6 | 3.5 | 4 |
| C | 50% Black PS-B | 5.5 5.4 | 5.5 | 7 |

The spread layers containing all (100%) of either of the black beads (coatings D or E) work equally well, absorbing 96% of the hemoglobin signal (4% is detectable). The coatings containing only 50% of the black PS-B beads (Coating C) were better than those having only 50% of the black PVM-B beads (Coating B), presumably due to their higher loading of carbon black.

EXAMPLE 2

Use of Black Beads in bead spreading layer (BSL) to reduce the deleterious effects of increased wash volumes)

The sensitivity of immunoassays can be increased by more efficiently removing the unbound label and interferents during the assay. The most obvious way of doing this, of course, is by washing with greater wash volumes after the incubating step. We have noticed, however, that since the wash fluid contains luminol and $H_2O_2$, use of larger wash volumes has been accompanied with stronger background signals. This example shows that black bead spread layers also unexpectedly help to control the background when larger wash volumes are employed in immunoassays.

Two sets of elements were prepared as in example 1. One element comprised a machine-coated spreading layer having the white beads designated as A (White BSL) in example 1. The other element comprised a hand-coated spreading layer having the black beads designated E (Black BSL) in example 1. Otherwise the elements were identical. Each element was washed with the chemiluminescent signal reagent/wash solution described in example 1 at a rate of 1 $\mu L/sec$, using a different volume of wash for each element to produce a series for each of the elements based on wash volume. Chemiluminescence was read as in example 1. The results are reported in Table II. It shows that the background signal for the black bead spreading layer is much lower and remains relatively flat with increasing wash volume. On the other hand the background signal of the white bead spreading layer is higher initially and increases to much higher levels with increasing wash volumes.

TABLE II

4 Minute Chemiluminescent Signal

| Wash Volume ($\mu L$) | White BSL | Black BSL |
|---|---|---|
| 10 | 0.224 | +.029 |
| 25 | 0.348 | -.016 |
| 50 | 0.399 | -.012 |
| 75 | 0.533 | +.012 |
| 100 | 0.601 | +.008 |

EXAMPLE 3

Chemiluminescence sandwich assay for Thyroid Stimulating Hormone (TSH) Using a multilayer immunoassay element with a black bead spreading layer versus white bead spreading layer)

Elements were prepared as in example 1 having either the white spread layer of example 2 or the black bead spread layer of example 2, except that the elements also included a separate receptor layer located between the spreading layer and the gel pad. The receptor layer had the following composition:

| Layer | Material* | Dry Coverage g/m² |
|---|---|---|
| Receptor Layer | TRIS (0.05 M, pH 8) | 0.06 |
| | Anti TSH Capture Antibody/Beads | 0.5 |
| | Polymer Binder) | 0.54 |
| | Triton X-100 | 0.02 |

The following reagents were provided for this example:
Amerlite Calibrators B through F for TSH Assays

| Calibrator | Concentration (mIU/L) |
|---|---|
| B | 0.125 |
| C | 0.75 |
| D | 4 |
| E | 20 |
| F | 100 |

Anti TSH Antibody/HRP Conjugate

This reagent is a conjugate of anti TSH antibody covalently bound to horseradish peroxidase (HRP) at a concentration of about 0.223 mg/mL ($1.5 \times 10^{-6}$ M) diluted to $5 \times 10^{-9}$ M with phosphate buffered saline (PBS) solution containing 0.01% bovine serum albumin (BSA).

Chemiluminescent (Luminol) Signal Reagent/Wash Fluid

This reagent/wash solution was prepared and used in exactly the same manner as Example 1.

Hemoglobin

A stock solution of 10 mg/mL of Sigma H7379 (hemoglobin) in water was diluted to 100 mg/dL in Amerlite TSH Calibrator B.

TSH Assay

The antibody/HRP conjugate (4 $\mu L$) was added to 36 $\mu L$ of one of the TSH calibrators (final conjugate concentration was $5 \times 10^{-10}$ M) and mixed. Ten $\mu L$ of the mixture was immediately spotted on one of the elements. The element was then incubated for 10 minutes at 37° C. in a Petrie dish set in a 37° C. water bath. The element was then washed with 100 $\mu L$ of the signal/wash reagent at a rate of 0.8 $\mu L/sec$. The resulting chemiluminescence was read from the element in a luminometer as in Example 1. Results are presented in Table III.

TABLE III

TSH Assay
4-Minute Chemiluminescence Signal

| | | White Bead Spread Layer | | | Black Bead Spread Layer | | |
|---|---|---|---|---|---|---|---|
| TSH Cali-brator | mIU/L | 2 Repli-cates | Mean | Signal/ Noise | 2 Repli-cates | Mean | Signal/ Noise |
| B | 0.125 | 5.3 6.4 | 5.9 | 1 | 0.215 0.212 | 0.214 | 1 |
| C | 0.75 | 4.9 5.9 | 5.4 | 1 | 0.336 0.303 | 0.32 | 1.5 |
| D | 4 | 9.4 10.8 | 10.1 | 1.7 | 1.05 0.91 | 0.98 | 4.6 |

TABLE III-continued

TSH Assay
4-Minute Chemiluminescence Signal

| TSH Cali- brator | mIU/L | White Bead Spread Layer | | | Black Bead Spread Layer | | |
|---|---|---|---|---|---|---|---|
| | | 2 Repli- cates | Mean | Signal/ Noise | 2 Repli- cates | Mean | Signal/ Noise |
| E | 20 | 67<br>64 | 65.6 | 11.1 | 8.7<br>9.1 | 8.9 | 41.6 |
| F | 100 | 404<br>380 | 392 | 66.4 | 66<br>65 | 66 | 308 |

The concentration of calibrator B was so low that it was considered to be zero for calculation of the signal/noise ratio. It is evident from Table III that the elements with the black bead spreading layers gave higher signal to noise ratios. The data in Table III were used to generate the dose/response curves. Although the slope of the dose/response curve for the black bead spreading layer elements was less than the slope for the elements with the white bead spreading layer, the former elements provided better sensitivity. If we define the detection limit to be two times the background (Table III: black=2×0.214 CL units, white=2× 5.9 CL units), the black bead elements have a detection limit of 2 mIU/L and the white 5 mIU/L. This represents a marked improvement in signal to noise ratio of the black bead spread layers over the white bead spread layers.

The invention has been described in detail with particular reference to preferred embodiments thereof, but it will be understood that variations and modifications can be effected within the spirit and scope of the invention.

We claim:

1. A competitive immunoassay for determining an analyte in a sample comprising hemoglobin and said analyte, comprising:
   a) providing a dry multilayer immunoassay element comprising in order,
      (i) a spreading layer comprising particles having a light absorbing material encapsulated therein,
      (ii) a receptor layer comprising an immobilized receptor which specifically binds to said analyte or an analog thereof, and
      (iii) a radiation-transmissive support;
   b) contacting the spreading layer with said sample;
   c) contacting the spreading layer with less than or about $5\times10^{-10}$ M label reagent comprising a peroxidase label conjugated to said analyte or an analog thereof;
   d) contacting the spreading layer with a solution comprising a chemiluminesence reagent admixture which reacts with the peroxidase label to produce a chemiluminescent signal and which is effective to separate unbound label reagent from label reagent bound to said immobilized receptor; and
   e) measuring the chemiluminescent signal produced by said bound label reagent to determine said analyte in said sample.

2. A competitive immunoassay for determining an analyte in a sample comprising hemoglobin and said analyte, comprising:
   a) providing a dry multilayer immunoassay element comprising in order,
      (i) a spreading layer comprising particles having a light absorbing material encapsulated therein,
      (ii) a conjugate layer comprising less than or about $5\times10^{-10}$ M label reagent comprising a peroxidase label conjugated to said analyte or an analog thereof,
      (iii) a receptor layer comprising an immobilized receptor which specifically binds to said analyte or an analog thereon, and
      (iv) a radiation-transmissive support;
   b) contacting the spreading layer with said sample;
   c) contacting the spreading layer with a solution comprising a chemiluminesence reagent admixture which reacts with the peroxidase label to produce a chemiluminescent signal and which is effective to separate unbound label reagent from label reagent bound to said immobilized receptor; and
   d) measuring the chemiluminescent signal produced by said bound label reagent to determine said analyte in said sample.

3. A sandwich immunoassay for determining an analyte in a sample comprising hemoglobin and said analyte, comprising:
   a) providing a dry multilayer immunoassay element comprising in order,
      (i) a spreading layer comprising particles having a light absorbing material encapsulated therein,
      (ii) a receptor layer comprising an immobilized receptor which specifically binds to said analyte or an analog thereof, and
      (iii) a radiation-transmissive support;
   b) contacting the spreading layer with said sample;
   c) contacting the spreading layer with less than or about $5\times10^{-10}$ M label reagent comprising a peroxidase label conjugated to a second receptor which specifically binds co said analyte;
   d) contacting the spreading layer with a solution comprising a chemiluminesence reagent admixture which reacts with the peroxidase label to produce a chemiluminescent signal and which is effective to separate unbound label reagent from label reagent bound to said immobilized receptor through said analyte; and
   e) measuring the chemiluminescent signal produced by said bound label reagent to determine said analyte in said sample.

4. A sandwich immunoassay for determining an analyte in a sample comprising hemoglobin and said analyte, comprising:
   a) providing a dry multilayer immunoassay element comprising in order,
      (i) a spreading layer comprising particles having a light absorbing material encapsulated therein,
      (ii) a conjugate layer comprising less than or about $5\times10^{-10}$ M label reagent comprising a peroxidase label conjugated to a receptor which specificall binds to said analyte,
      (iii) a receptor layer comprising an immobilized second receptor which specifically binds to said analyte, and
      (iv) a radiation-transmissive support;
   b) contacting the spreading layer with said sample;
   c) contacting the spreading layer with a solution comprising a chemiluminesence reagent admixture which reacts with the peroxidase label to produce a chemiluminescent signal and which is effective to separate unbound label reagent from label reagent bound to said immobilized second receptor through said analyte; and
   d) measuring the chemiluminescent signal produced by said bound label reagent to determine said analyte in said sample.

* * * * *